United States Patent [19]

Good

[11] Patent Number: 4,711,764

[45] Date of Patent: Dec. 8, 1987

[54] AUTOMATIC SAMPLE INJECTOR AND DISPOSABLE SAMPLE CASSETTE

[75] Inventor: Thomas J. Good, Sierra Madre, Calif.

[73] Assignee: Analytichem International, Inc., Harbor City, Calif.

[21] Appl. No.: 790,861

[22] Filed: Oct. 24, 1985

Related U.S. Application Data

[63] Continuation of Ser. No. 433,514, Oct. 8, 1982, abandoned.

[51] Int. Cl.$^4$ ............................................. G01N 31/08
[52] U.S. Cl. ........................................ 422/65; 55/386; 73/61.1 C; 422/70; 436/161
[58] Field of Search .......... 55/386; 73/864.85, 61.1 C; 210/198.2; 422/63–67, 70, 102, 104

[56] References Cited

U.S. PATENT DOCUMENTS 4,289,620 9/1981 Hara ................................. 422/70 X Primary Examiner—Barry S. Richman
Assistant Examiner—Michael S. Gzybowski
Attorney, Agent, or Firm—Stanley Z. Cole; Gerald M. Fisher; David Schnapf

[57] ABSTRACT

An automatic sample injector for high pressure liquid chromatography, utilizing a cassette-like holder of a plurality of sample columns and an automatic injection unit which sequentially and successively advances the cassette and removes each sample therefrom in accordance with the test to be conducted on the sample. The cassette-like sample carrier utilizes a plurality of sample columns disposed in line with each other, with the body of the cassette being unsymmetrical to prevent reversal thereof in the injection machine. The injection machine, when a sample cassette is placed thereon, automatically advances the cassette to the first sample column, connects the column to the chromatographic or other system, removes the sample therefrom, decouples the sample tube from the system and again advances the cassette to the next sample tube therein for similar processing thereof. The injection apparatus engages the cassette in a manner to sequentially provide positive sealing for each sample tube therein and support for that tube so that high pressures may be used in conjunction with a plastic cassette without requiring the cassette to support such pressures and without requiring additional special seals with respect thereto.

5 Claims, 14 Drawing Figures

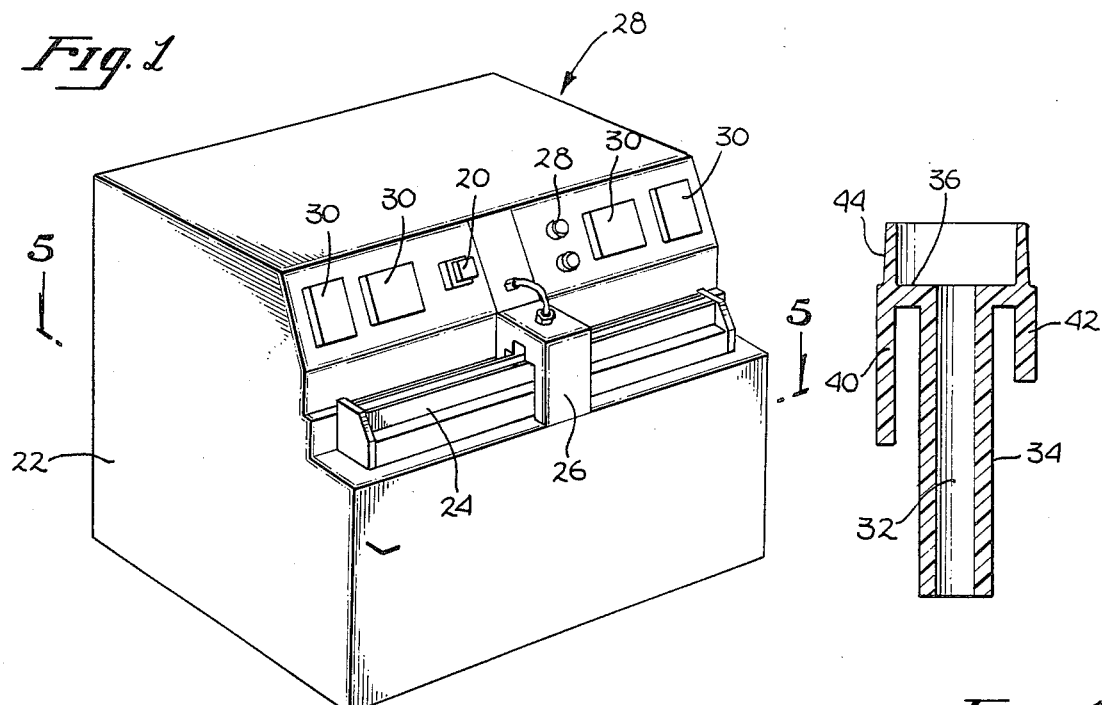
Fig. 1
Fig. 4
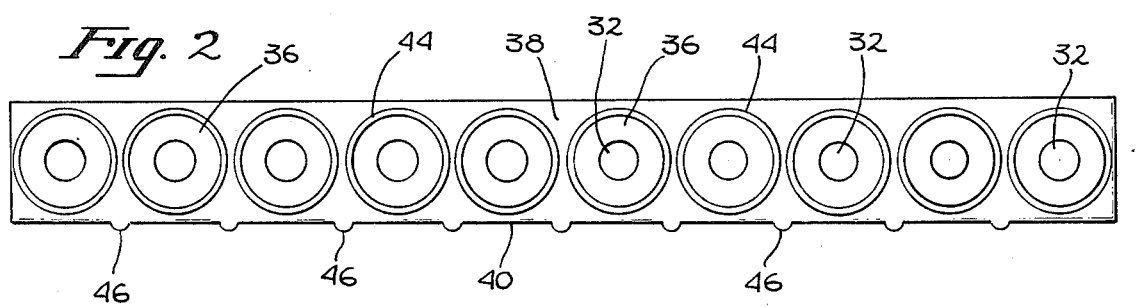
Fig. 2
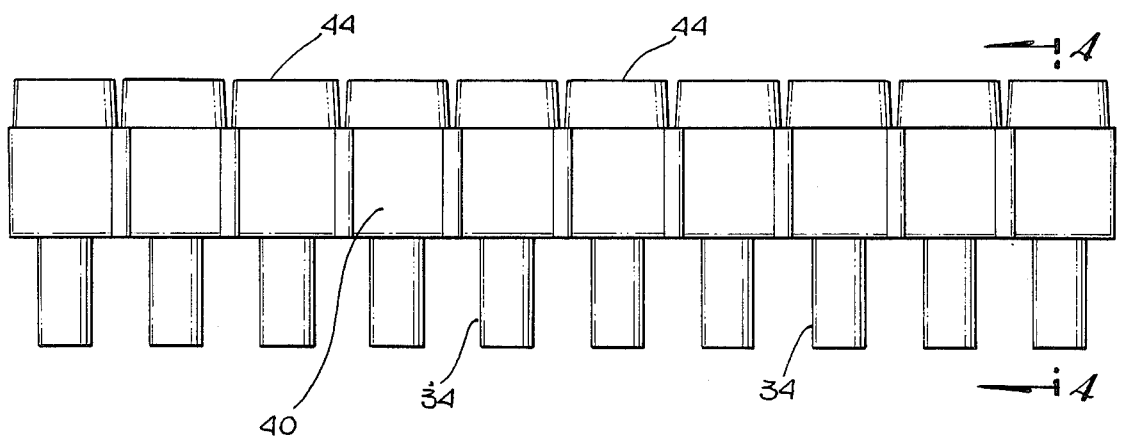
Fig. 3

AUTOMATIC SAMPLE INJECTOR AND DISPOSABLE SAMPLE CASSETTE

This is a continuation of application Ser. No. 06/433,514 filed 10/8/82, now abandoned.

BACKGROUND OF THE INVENTION

1. Field of the Invention

The present invention relates to the field of sample injection equipment, and more particularly to sample injection equipment which may be used in high pressure liquid chromatography and similar fields.

2. Prior Art

The preferred embodiment of the present invention is directed toward the field of high pressure chromatography, and accordingly the prior art relating specifically thereto shall be described, it being understood however, that the present invention is not to be so limited as it may be readily used for other purposes such as UV spectriphotometric instrumentation and gas chromotography.

In high pressure chromatography, separating columns are first prepared having a special sorbent material therein for removing selected organic compounds from a sample passed therethrough. Such separating columns with various sorbent materials therein are commercially available from Analytichem, the assignee of the present invention. In the prior art, the separating columns characteristically are metal tubes of some form having a fixed filter at each end to confine the special sorbent therein against the relatively high pressure to which they will be subjected. To test for a particular material, a sample is first passed through the sample column to retain the selected organic material thereon, thereby effectively concentrating the material to be tested for. Thereafter the sample column is placed in the high pressure system, and the sample removed with an appropriate solvent under high pressure to carry the sample to the chromatograph. Such systems and testing are well known in the prior art, being commonly used in medical and other applications. However, heretofor the preparation and evaluation of the samples was generally a manual task requiring substantially constant attention of an operator, and providing all of the normal opportunities for operator error, including nonuniformities in the test method and/or the misidentification or intercontamination of samples.

Various methods and apparatus have been proposed to at least partially automate chromatographic testing, such as disclosed in U.S. Pat. No. 3,583,230 entitled "Sample Injection Method and Apparatus". In accordance with that patent, injector cartridges having filter material are placed in receiving holes around the periphery of a rotating turn table after a sample has been centrifuged into the filter material and the sample is filtered during the centrifuging. The sample within the cartridge is preeluted and then the turn table is rotated sequentially positioning the cartridges beneath an extendable and retractable loader which engages the cartridge. Desired zones of the chromatographic spectrum of the preeluted sample are injected through a capillary outlet in the cartridge into a chromatographic system. The cartridges themselves are individual cartridges having an elongated housing of plastic or other suitable material with a chamber or elongated channel formed centrally therein, lined with a tubular support column of glass or suitable plastic material for supporting the chromatographic absorptive filter material. That system has the advantage of providing automatic sealing on the cartridge wherein a plurality of samples can automatically and sequentially injected into a chromatographic system in such a manner that the chromatographic column apparently can be used continuously without regeneration. However, because the sample cartridges are individual sample cartridges, operator attention is required for the loading and unloading of the individual cartridges, with the attendant opportunities for misidentification of test results as a result thereof.

U.S. Pat. No. 3,996,017 discloses a cassette separating column system for chromatography wherein each cassette-like device contains a separating column with appropriate coupling means at each end thereof for connection to complimentary shaped fittings in a fluid tight manner. A special connection fitting allows the direct connection of the conical coupling surfaces to two column-containing cassettes simultaneously, though as before, each cassette itself only contains a single column, whereby each individual cassette and therefore each individual column would require manual loading, also with the same opportunity for confusion of samples.

Finally, U.S. Pat. No. 3,860,393 entitled "Automated System for Identifying Traces of Organic Chemical Compounds in Aqueous Solutions" discloses a system wherein a single sample may be automatically analyzed to identify traces of organic chemical compounds of different types. Here again, the system envisions a single sample containing column, even though multiple tests may be conducted on the sample.

BRIEF SUMMARY OF THE INVENTION

An automatic sample injector for high pressure liquid chromatography and the like, utilizing a cassette-like holder of a plurality of sample columns and an automatic injection unit which sequentially and successively advances the cassette and removes each sample therefrom in accordance with the test to be conducted on the sample. The cassette-like sample carrier utilizes a plurality of sample columns disposed in line with each other, with the body of the cassette being unsymmetrical to prevent reversal thereof in the injection machine. The injection machine, when a sample cassette is placed thereon, automatically advances the cassette to the first sample column, connects the column to the chromatographic or other system, removes the sample therefrom, decouples the sample tube from the system and again advances the cassette to the next sample tube therein for similar processing thereof. The injection apparatus engages the cassette in a manner to sequentially provide positive sealing for each sample tube therein and support for that tube so that high pressures may be used in conjunction with a plastic cassette without requiring the cassette to support such pressures and without requiring additional special seals with respect thereto.

BRIEF DESCRIPTION OF THE DRAWINGS

FIG. 1 is a perspective view of the preferred embodiment of the present invention.

FIG. 2 is a view of a preferred sample column cassette used for the preferred injector of the present invention.

FIG. 3 is a front view of the cassette of FIG. 2.

FIG. 4 is a cross section of a sample column in the cassette taken along line 4—4 of FIG. 3.

FIG. 11 is a block diagram of the injector control system.

DETAILED DESCRIPTION F THE INVENTION

Figure 5:
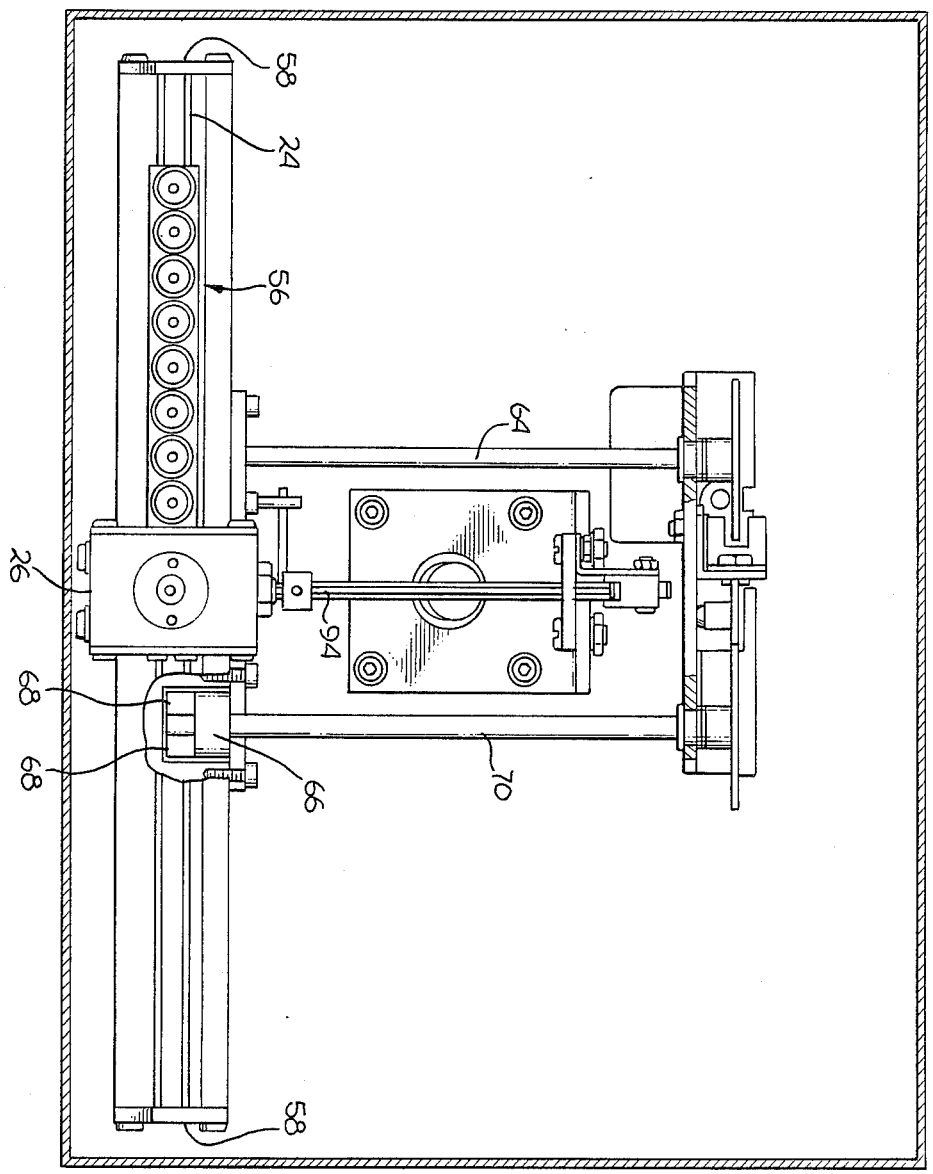
FIG. 5 is a top view of the mechanism of the injector of FIG. 1.

The preferred embodiment of sample injector of the present invention may be seen in FIG. 1. The injector, generally indicated by the numeral 20, is characterized by a housing 22 with a track-like region 24 at the front thereof extending generally across the width of the housing. At the center of the track 24 is a bridge-like region 26 which, as will subsequently be described in detail, is the region in which sample injection takes place. Also disposed on the face of the sample injector 20 above track 24 are control switches 28 and various indicator lights 30, indicating the status of the machine throughout its sequence of operation.

Now referring to FIGS. 2, 3 and 4, the preferred form of cassette used with the sample injector of FIG. 1 may be seen. FIG. 2 is a top view of the cassette with FIG. 3 being face view thereof and FIG. 4 a cross section taken along line 4—4 FIG. 3. In the preferred embodiment, each cassette contains 10 sample columns 32, each defined in part by a downward extending cylindrical projection 34 joined at the tops thereof by integral flange-like regions 36, top plates 38 and forward and rear faces 40 and 42 respectively. Concentric with each column 32 and the cylindrical region 34 is a large diameter upward extending cylindrical region 44 associated with each column. Cylindrical regions 44 are provided to conveniently engage and seal against a sample preparation manifold-like member to aid in the retention of the chemical isolates from the sample by providing temporary recepticles for the isolates as they slowly pass through the sample columns.

It may be seen from FIG. 4 that the forward face 40 and rear face 42 are substantially different size, the forward face 40 extending downward approximately twice as far as the rear face. Also, as may be seen in FIGS. 2 and 3, the forward face 40 has protrusions 46 thereon midway between sample columns, which protrusions serve a number of functions. First, of course, they separate the sample columns to define a region therebetween on which sample identifications may be placed, if desired. They also provide a gross difference in the feel of the forward and rear faces so that an operator can readily orient the cassette by feel as well as by sight. Finally, the difference in size of the forward and rear faces provides the positioning key which assures proper cassette orientation when the cassette is inserted into injector 20.

Now referring to FIGS. 5 through 10, various views of the injector 20 of FIG. 1 with the cover removed (or cut away) may be seen. In the description to follow, references will be made to certain of these figures for illustration of specific points, though in many cases one or more of the parts described or even the entire subassembly being described may be visible in one or more other figures also.

Figure 6:
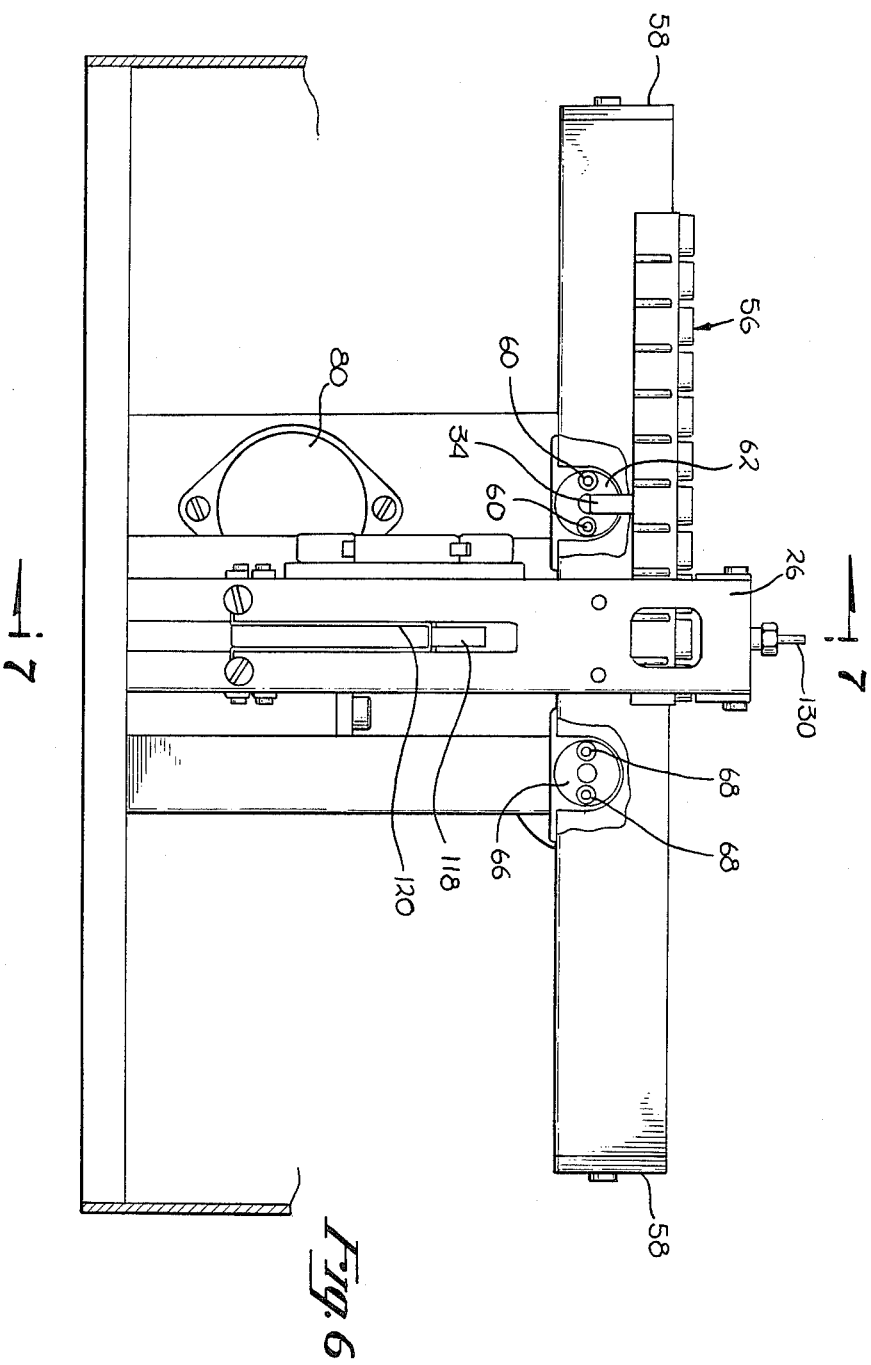
FIG. 6 is a front view of the mechanism of the injector of FIG. 1.
Figure 7:
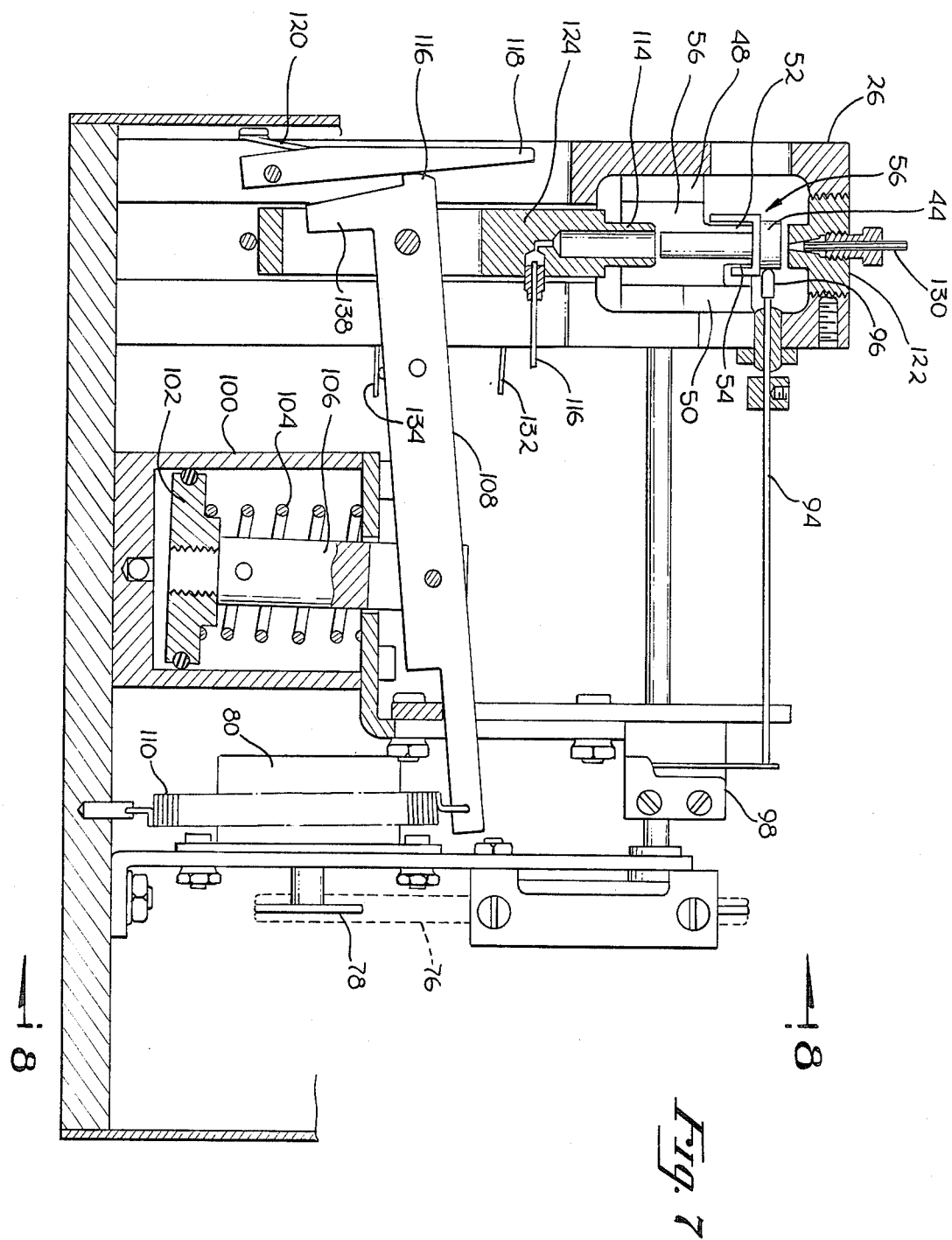
FIG. 7 is a partial cross section taken along line 7—7 of FIG. 6.

The track-like region 24 of FIG. 1 is visible also in the top view of FIG. 5 and in cross section in the view of FIG. 7. As may be seen in FIG. 7, the track is comprised of a pair of members 48 and 50, each having an upward extending cassette guide rail 52 and 54, respectively. The guide rails 52 and 54 shown in FIG. 7 are not shown in cross section as they are interrupted at that particular cross section by a vertical hole-like opening 56 therethrough. It will be noted that guide rails 52 and 54 are of different length and cooperate with forward and rear faces 40 and 42 (see FIG. 4) of the cassette so as to allow a cassette, such as a cassette generally indicated by the numeral 56 in FIG. 7, to rest on the guide rails with only orientation, i.e. to not properly rest on the guide rails if the cassette is flopped end for end. The members 48 and 50 are in turn supported by the structure supporting bridge 26 at the center of the machine, and at the ends by end support plates 58, visible in FIGS. 5, 6 and 8. The track projections 52 and 54 are of sufficient length so as to support the entire length of a cassette at the left of bridge 26, as well as at the right of bridge 26, so that a cassette may be easily placed on the track at the left of bridge 26, the normal loading station for the preferred embodiment, or removed from the track to the right of bridge 26, the normal unloading position for a cassette in the preferred embodiment disclosed herein. The members 48 and 50, as well as the track-like projections 52 and 54 thereon have a sufficient separation, of course, to allow the free sliding of the cylindrical downward projection 34 (see FIGS. 3 and 4) on each cassette so that nothing on members 48 and 50 will interfere with the free sliding of a cassette anywhere along their entire length.

When a cassette such as cassette 56 is loaded into the left side of the track-like region 24, one of the downward projecting cylindrical regions 34 of the cassette will extend between pins 60 on wheel 62, as may be seen in FIG. 6. The axis of the shaft 64 supporting wheel 62 from which pins 60 extend is at a level substantially equal to the level of the bottom of projections 34 on the cassette so as to positively entrap the downward projection 34 forming that particular sample column. A similar wheel 66 (see FIG. 6 again) supporting pins 68 is positioned on shaft 70 (see FIG. 5) spaced at the opposite side of bridge 26. More particularly, it may be seen from FIGS. 2 through 4 that the spacing from the center line of one column on a cassette to the center line of either adjacent column is a fixed spacing, i.e. the columns are equally spaced along the cassette. Shaft 64 of FIG. 5 is spaced to one side of the center line of bridge 26 by a distance equal to an integer times the column to column center line spacing of a cassette, whereas the center line of shaft 70 is located a similar distance at the opposite side of the center line of bridge 26. Furthermore, the spacing between shafts 64 and 70 is less than the overall length of an individual cartridge so that pins 68 on wheel 66 will engage one of the tubular projections 34 on a cartridge while another corresponding portion of the same cartridge is still engaged by pins 60 of wheel 62.

Shafts 64 and 70 are driven in rotation by sprockets 72 and 74 respectively (see FIG. 8), in turn driven by a chain 76 and drive sprocket 78 on a stepper motor 80 (see FIG. 7). A tension is maintained in chain 76 by a spring loaded idler 82, supported on arm 84, pivoted at pin 86 and urged against the chain by coil spring 88. When the stepper motor is driven in what constitutes a forward direction, both wheels 62 and 66 (see FIG. 6) are driven in unison. For the position of the cassette shown in FIG. 6, as wheel 62 rotates in a clockwise direction as viewed in that figure, pin 60 effectively moves downward and under the bottom of column 34 between the pins while pin 60 moves upward in an arc, curving to the right to advance the cassette by one sample column for each 180 degree rotation of the wheel. It will be noted that if the stepper motor were to rotate at a uniform drive speed, wheel 62, as well as wheel 66, would also turn at a uniform speed, but the cassette itself would move in a sine wave fashion, accelerating to a maximum velocity and then decelerating to a stop when the wheels pass through the position shown in FIG. 6, which of course corresponds to the alignment of a sample column (actual or theoretical) with the center line of bridge 26. Because the velocity of the cassette is zero for the wheel position shown in FIG. 6, some slight error in wheel stopping position can be tolerated while still accurately aligning a sample column on the cassette with the center of the bridge. In that regard, wheel 74 (see FIG. 8) has two diametrically opposed alignment holes 90 therethrough, only one of the holes being visible in that figure which may be sensed by the LED-photosensor combination 92 to provide an electrical signal indicative of the arrival of the sprocket at a desired stopping position.

In addition to the foregoing, there is a feeler bar 94, shown in FIGS. 5 and 7, having a tip 96 thereon for sensing the arrival of a sample column on the cassette at the center line of the bridge-like member 26 by sensing the cylindrical regions 44 of each column and actuating a switch 98 in response thereto. Thus when a cassette is first inserted and the unit turned on, stepper motor 80 will be advanced, advancing the cassette until the first column is sensed under the bridge, at which time the stepper motor will be stopped when sprocket 74 reaches the desired stopping position as indicated by the photosensor 92.

Figure 9:
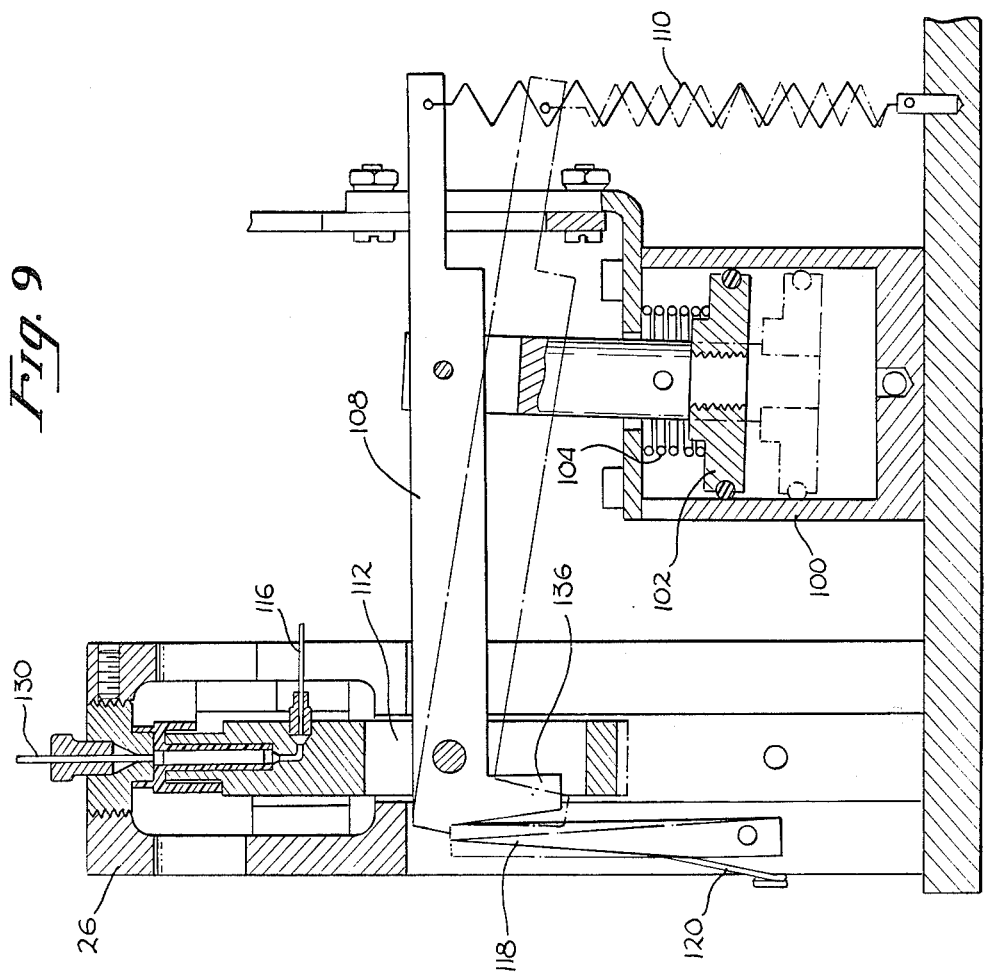
FIG. 9 is a view similar to FIG. 7 illustrating the operation of a mechanism to seal on a sample column in a sample column cassette of the present invention.
Figure 7:
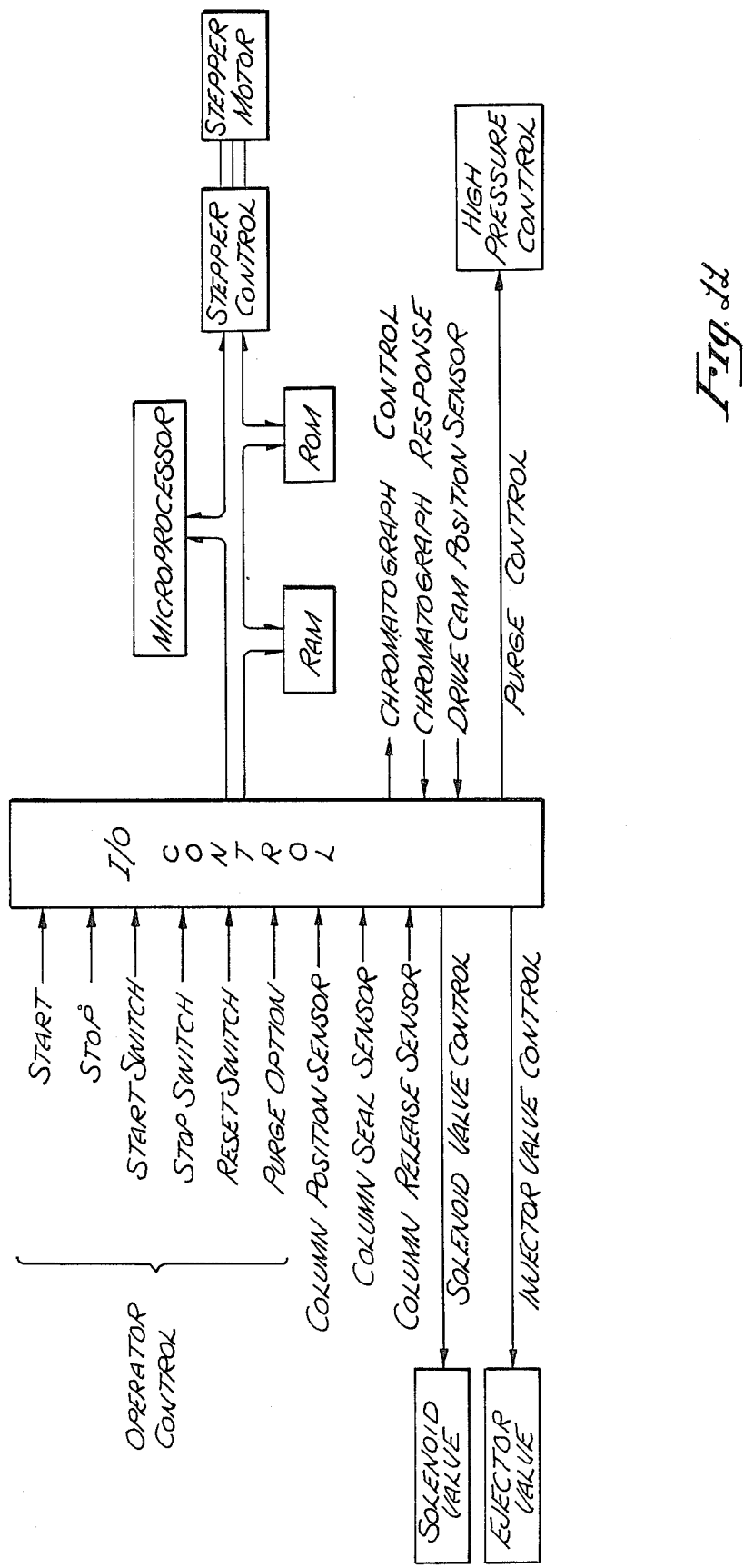

At this point in the operation of the system, a solenoid valve is actuated to provide air pressure to the pneumatic cylinder 100, forcing piston 102 therein upward against coil spring 104 (see FIG. 7 and particularly FIG. 9). The push rod 106 of piston 102 is pivotally connected to bar 108, yieldably held down at one end by coil spring 112 and pivotally coupled to a piston-like slide member 112 adjacent the other end. The slide member 112 has an upward extending hollow cylindrical projection 114 for sliding over the downward projecting portion 34 of a sample column aligned therewith, with the hollow portion being in fluid communication with a small flexible metal tube 116. In the preferred embodiment metal tube 116 is a fine diameter metal tube having substantial flexibility as a result of a coil put in the tube for this purpose, not shown in the drawing.

Normally the projection 114 is at an elevation below the bottom of the sample columns on a cassette. However as pressure is applied to the cylinder 100 and piston 102 starts upward as shown in FIG. 9, the left end of bar 108 and piston member 112 move upward, the right end of the bar being retained in the lower position by the coil spring 110. As the left end of bar 108 encounters resistance to further upward movement by the engagement of the upward projecting protrusion 114 on piston-like member 112 with the bottom of the flange 36 on the bottom line sample column, the right hand of bar 108 rises against the spring 110, so that end tab 116 reaches over the top of linkage pawl 118 spring loaded toward the right by pawl spring 120. Bar 108 effectively becomes a pry bar against the linkage pawl 118 to force piston-like member 112 upward for a short additional distance with a very high force. The result of this action may be seen in FIG. 10. In particular, top piece 122, threaded into bridge member 26 to the desired depth, fits within the upward cylindrical projection 44 on the aligned sample column, and is provided with a sharp downward projection 124 for positively biting into the top of flange 36 on that sample column. Similarly the upward projecting member 114 has a sharp upward projecting ring 128 for biting into the bottom of the flange 36, thereby providing a high integrity, high pressure seal against the plastic without the use of O-rings or other special sealing members. The deformation caused by the biting action of the projecting rings does not preclude resealing the plastic cassette by multiple re-insertions of the same cassette. Reinsertion of the cassette will be necessary in order to selectively elute molecular classes of chemical isolates by serially changing chromatographic conditions if more than one class of isolates were retained on the cassettes. Of course, now the sample column is in direct communication with the fluid lines 116 and fluid line 130 coupled to a sample injection valve.

As a safety feature, a pair of switches 132 and 134 (see FIG. 7) are provided to sense when arm 108 is at the proper extremes of its motion. In particular, switch 132 senses when the piston number 112 is in fully upward and sealed position, whereas switch 134 senses when the piston member is fully down to allow the advancement of the cassette to the next sample column position. In that regard it should be noted that as the cylinder pressure is relieved, the right end of bar 108 starts downward, with the downward projection 136 of bar 108 pushing the linkage pawl 118 toward the left as referenced in FIGS. 7 and 9 to release the left end of bar 108 from the linkage pawl, allowing it to return to the lower position under the influence of spring 104 in the cylinder.

Now referring to FIG. 11, a block diagram of the injector control system may be seen. The control system in the preferred embodiment is microprocessor based. The microprocessor 140 is provided with a random access memory 142 (RAM) for temporary data storage and a read only memory 144 (ROM) for permanent program storage. In addition to the RAM and ROM on the microprocessor bus are input/output controls 146 and a stepper motor control 148 for driving the stepper motor 80. Typically the input/output controls 146 comprise decoders and latches so that any of the desired input or output signals may be addressed and read or written to at any time under microprocessor control. The organization of such microprocessor control systems is very well known in the prior art and may generally be found in substantially any text book on the subject, and also in microprocessor manufacturers' literature. The difference between various control systems normally is concentrated in the size of the read only memory and random access memory required to store and execute the desired program, the number of input and output signals which must be handled by some form of I/O control and any special output signals such as stepper motor sequencing as used in the present invention.

In the preferred embodiment, various operator controls are provided for the convenience of the operator. In particular, since each cassette in the preferred embodiment comprises ten sample columns, tests may be conducted on a cassette using less than all of the ten columns. By way of example, one might use columns 1 through 4 on a particular cassette at one time and later use columns 5 through 10. Accordingly, the preferred embodiment includes a provision for the operator to select a starting column number and an ending column number, either of which may be set from 1 and 10. As shall subsequently be seen, the microprocessor control system will sense when an ending number has been set to less than the starting number to indicate an error to the operator before proceeding with the testing. In addition, of course, the operator has the normal controls available for such equipment, such as a start switch, a stop switch and reset switch. The operator also has the option of adding a solvent purge cycle to the overall operation. A suitably selected solvent which will not elute the retained chemical isolates will be injected through the column in the pressure chamber in order to purge the column (specifically the solid sorbent therein) of entrapped air.

Figure 8:
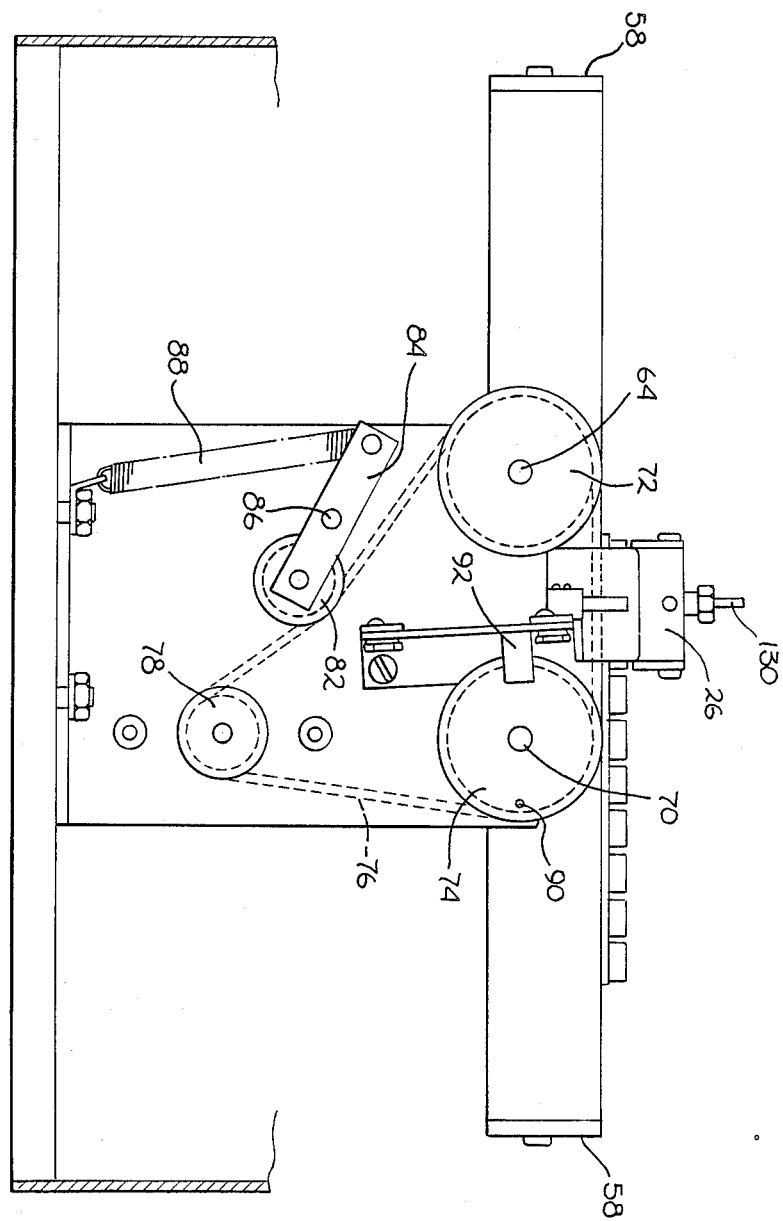
FIG. 8 is a view taken along line 8—8 of FIG. 7.
Figure 10:
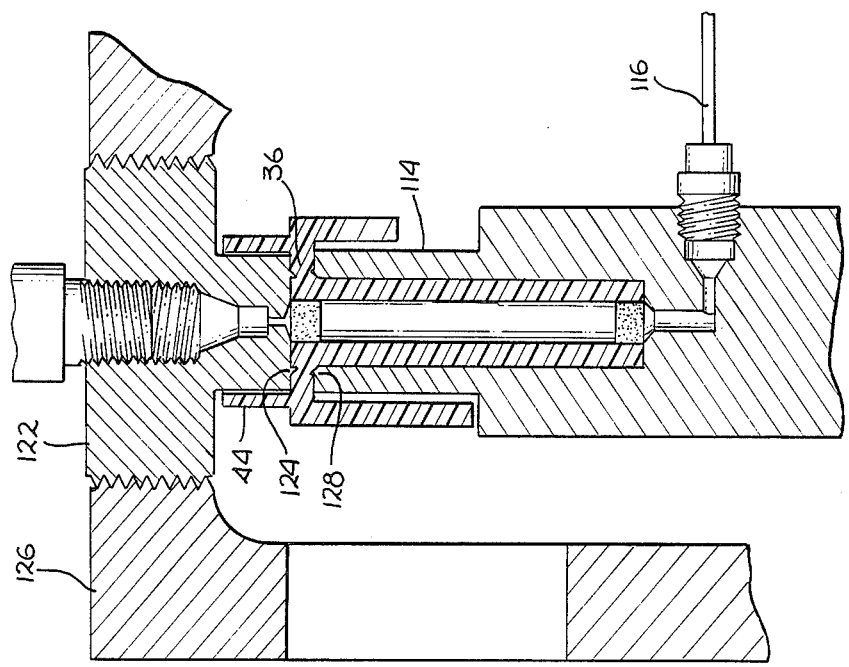
FIG. 10 is a view of a portion of FIG. 9 taken on an expanded scale to better illustrate the sealing.

The other inputs identified for the I/O controls 146 in FIG. 11 is a column position sensor corresponding to switch 98 (FIG. 7), a column seal sensor corresponding to the switch 112, a column release sensor corresponding to switch 134 (both switches being also shown in FIG. 7), a chromatograph response signal to indicate the completion of a test by the chromatograph, and a drive position sensor signal corresponding to the photosensor output of photosensor 92 (FIG. 8). The outputs from the I/O controls include a chromatograph control, i.e. start signal, a solenoid valve control for a solenoid valve 150 to control the pneumatic cylinder 100 (FIG. 7), and finally, an injector valve control, also a solenoid valve to control the injector valve 152 to couple the column in the test position to the liquid chromatograph (such valves are well known in the prior art, being readily available from a number of manufacturers including Rheodyne Incorporated of Cotati, Calif.).

Figure 12A:
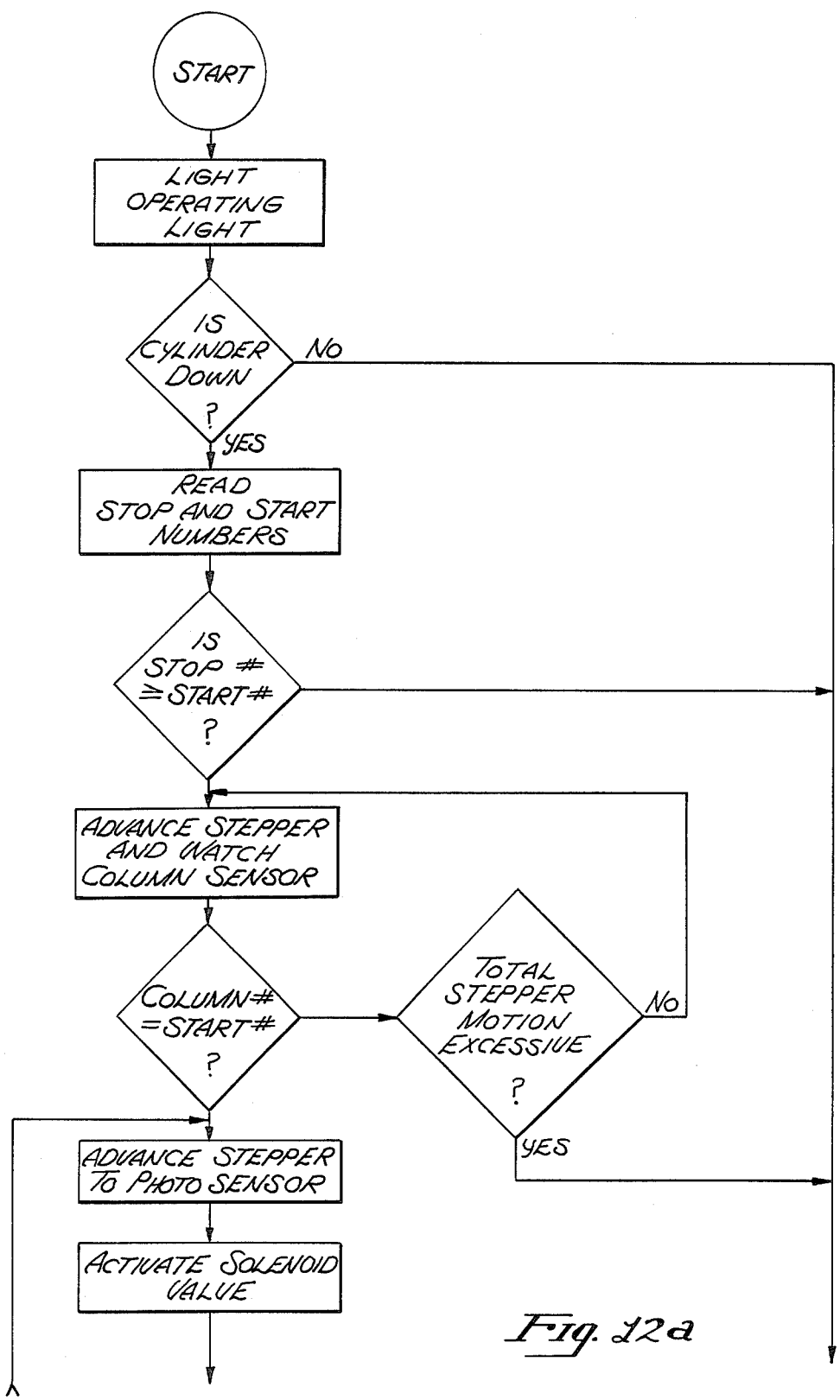
FIG. 12, comprising three sheets identified as FIGS. 12a, 12b and 12c, is a logic flow diagram of the control system of FIG. 11, FIG. 12a being the top portion of the diagram, FIG. 12b being the center portion and FIG. 12c being the lower portion thereof.
Figure 12B:
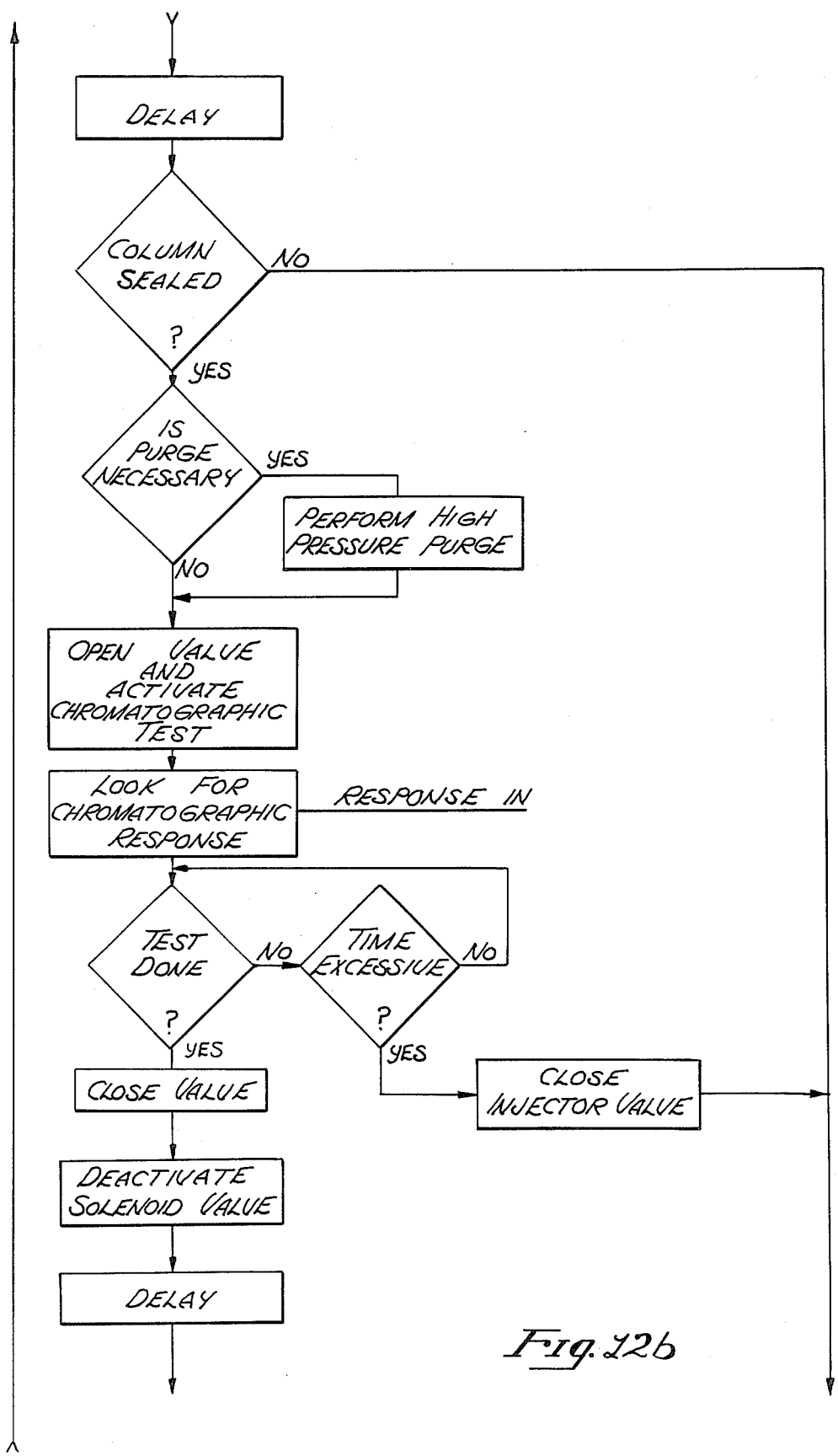
Figure 12C:
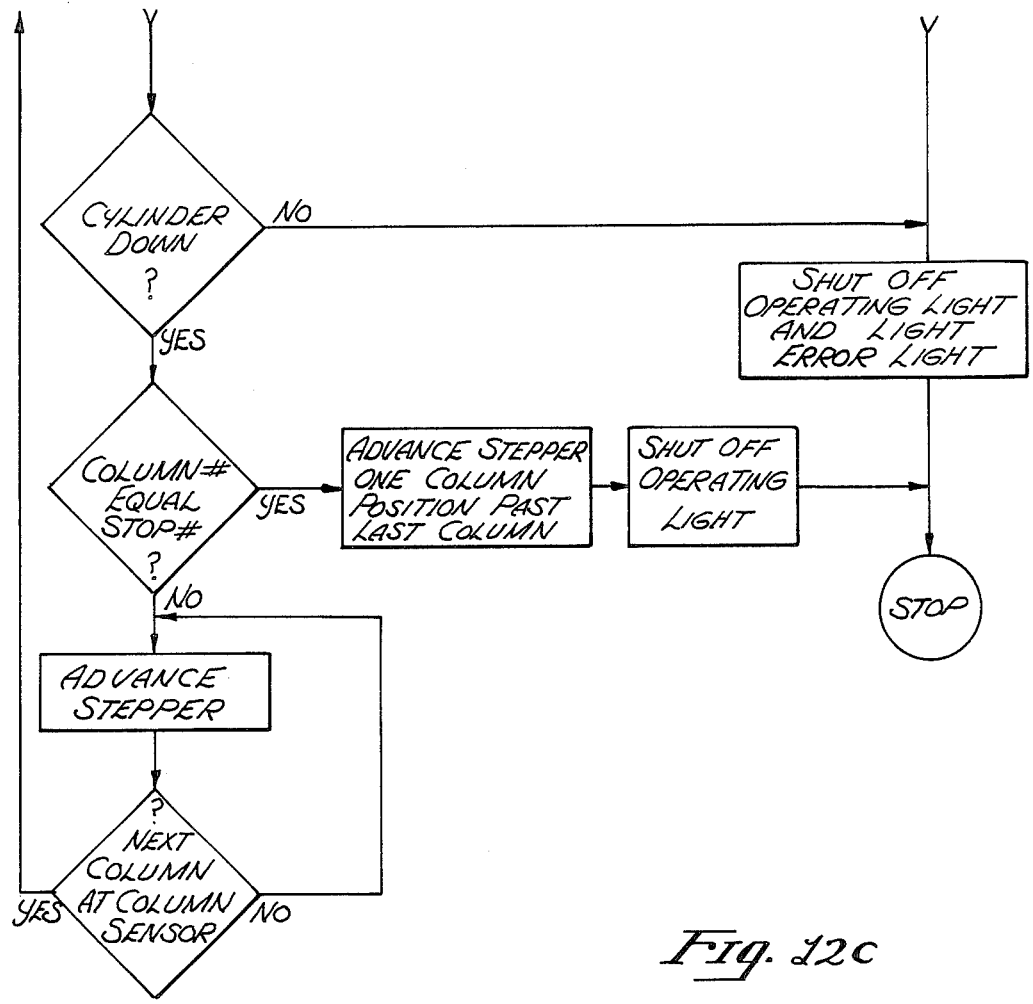

A logic flow diagram for the operation of the system may be seen in FIG. 12. After the operator loads a cassette into the machine and sets the start and stop number, the start button is pushed. This causes the control system to turn on an operating light, and then test switch 134 to be sure that the mechanism is in the proper operating position with piston 102 of cylinder 100 in the down position. If it is not, the operating light is shut off and an error light is turned on, after which time further operation is stopped. Assuming that the cylinder is down as desired, the system reads in the start number and stop number previously set by the operator and tests these two numbers to make sure that the stop number is equal to or greater than the start number. If it is not, again the error sequence hereinbefore described is executed. Assuming that the stop number is equal to or larger than the start number, the stepper motor is advanced as the system watches the column sensor switch 98. The stepper motor is continually advanced until either the column sensor switch indicates that the desired column is approaching the test position, or until the total stepper motor motion is excessive, indicating some form of malfunction, or the absence of a cassette in position when the start button was pushed.

As the desired column approaches the test position as sensed by switch 98, the stepper is continued to be advanced until photosensor 92 indicates that the column has reached the test position. Thereafter the solenoid valve controlling the supply of air to cylinder 100 is activated to carry out the column sealing operation. After sufficient delay to enable the sealing to be accomplished, switch 132 is sampled to make sure that the column is sealed. If the column is not sealed, the error sequence is again executed. Assuming however, that the column is properly sealed, the purge segment of the injection cycle is executed. If the operator has selected this option, a high pressure injection of a solvent in the amount set by the operator is performed in order to purge entrapped air from the column sorbent material. This solvent is selected so that the retained isolates are not eluted. The purge is readily accomplished by commercially available high pressure, air activated syringes. The solenoid valve controlling the sample injector valve is actuated and a signal is provided to the chromatograph to proceed with the chromatographic testing. When the test is completed, the injector valve is then closed and the solenoid valve controlling the pressurized air to cylinder 100 is closed, thereby releasing the sample column just tested. The determination of a test being completed may be by way of simple time delay, or as shown in FIG. 12, by way of a response from the chromatograph, in which case a failure thereof may also be indicated by an excessive test time, whereupon the system will close the injector valve and execute the error sequence.

Assuming that the tests have proceeded without incident and the cylinder 100 has been depressurized, after a sufficient delay the system then tests switch 134 to make sure that the cylinder is down, after which time the present column number is compared with the stop number previously set by the operator. If the two numbers are equal, the stepper motor is advanced one column position past the last column in the cassette as indicated by switch 98, after which time the operating light is shut off and the system is stopped. If the present column number is less than the stop number, the stepper is advanced until the next column approaches the test position as sensed by the column sensor switch 98, after which the operating sequence returns as indicated in FIG. 12 to the point where the column to be tested is brought into accurate alignment with the test position, and the test sequence hereinbefore described is sequentially repeated until the last column to be tested has in fact been tested.

There has been described herein a new and unique multiple sample column cassette for high pressure chromatography and the like, together with an automatic sample injection system for automatically and sequentially testing any or all of the columns in the cassette. Aside from the convenience and minimal operator attention required because of the automatic sealing and testing capability of the injector, the use of the present invention results in a grossly reduced opportunity for operator error. This is true not only because much of the testing sequence and timing thereof is accomplished under machine control rather than operator control, but also because once the samples to be tested have been properly prepared, the sample columns cannot be intermixed or confused as individual sample columns can. In that regard one might choose to prepare a known sample in column 1 and another known sample in column 10, by way of example, whereby test results identifying the known samples of columns 1 and 10 provide a very high degree of reliability in the proper testing of the intermediate sample columns. Further, the sealing method used with the present invention is particularly advantageous as it is not only of relatively low cost because of the absence of O-rings, pressure tight fitting of conical surfaces, etc., but also because the seal rings which bite into the flanges on each sample column during sealing leave tell-tale markings on the sample columns, thereby providing a very quick visual method of determining which cassettes and which columns on the cassettes have been tested.

Of course while the preferred embodiment of the present invention has been disclosed and described with respect to high pressure chromatography, it is to be understood as stated before, that the invention is in no way limited to any such testing as the concepts of the present invention may readily be applied to automate other forms of testing by those of reasonable skill in the art without departing from the spirit and scope of the invention.

I claim:

1. For use in an automatic sample injector for high pressure chromotography, the combination comprising:
    a unitary molded plastic sample holder having a plurality of integral cylindrical sample columns disposed in a row therein open at both ends thereof and being supported in the sample holder by a single common flange surrounding each sample column, said flange disposed adjacent one end of said sample columns;
    receiving means for receiving said sample holder;
    sealing means for controllably sealably engaging one of said plurality of sample columns at said single common flange and for releasing said sample column for controlled communication with each open end thereof, said sealing means having a substantially rigid top member and bottom member for directly engaging and pressing into opposite surfaces of said flange adjacent to and integral with said sample column to provide a positive sealing grip with each of the opposite surfaces of the flange to allow high pressure sample extraction from sample column said bottom member enclosing a lower portion of said sample column when engaging said flange to aid in the containment of high pressures;
    advancing means for controllably advancing said unitary sample holder along said receiving means to sequentially bring each of said plurality of sample columns on said unitary holder into alignment with said sealing means; and
    control means coupled to said sealing means and said advancing means for sequentially causing said advancing means to repetitively and sequentially (i) advance said sample holder to a next sample column, (ii) cause said sealing means to sealably engage the two opposite surfaces of the flange said of next sample column for sample extraction, and (iii) to release said next sample column in readiness for repetition of the sequence.

2. The combination of claim 1 wherein said receiving means will only receive a sample holder with a fixed predetermined orientation.

3. The combination of claim 1 wherein said receiving means comprises a track-like structure on which a sample holder may slide.

4. The combination of claim 1 wherein said common flange of said sample holders is adjacent the top thereof, said individual sample columns extending downward therefrom defining tubular sample columns, and
    said top member of said sealing means comprises a stationary upper sealing means for pressing into the top of said flange surrounding a sample column
    said bottom member of said sealing means comprises a moveable lower sealing means for controllably pressing into the bottom of said flange surrounding a sample column to trap said flange in compression between said upper and lower sealing means, said lower sealing means being vertically moveable between an upper sealing position and a lower release position by a distance exceeding the downward extension of said sample columns to provide clearance for the operation of said advancing means.

5. The combination of claim 4 wherein said sealing means further includes actuating means for causing movement of said lower sealing means comprising
    an actuator having an actuator element moveable between first and second actuator positions and
    mechanical means coupling said actuator element and said lower sealing means, said mechanical means being a means for causing, large motion movement of said lower sealing means from said lower release position toward said upper sealing position as said actuator element moves from said first actuator position toward said second actuator position, and small motion movement of said lower sealing means to said upper sealing position as said actuator element proceeds to said second actuator position.

* * * * *

UNITED STATES PATENT AND TRADEMARK OFFICE
CERTIFICATE OF CORRECTION

PATENT NO. : 4,711,764

DATED : December 8, 1987

INVENTOR(S) : THOMAS J. GOOD

It is certified that error appears in the above-identified patent and that said Letters Patent is hereby corrected as shown below: On the title page On page 1, in the section labelled Inventor, after the word "Calif.", please add:

--Paul W. Kercher, Pennsylvania Furnace, Pennsylvania; Stanley A. Stone, State College, Pennsylvania--

Signed and Sealed this

Eighth Day of November, 1988

Attest:

DONALD J. QUIGG

*Attesting Officer*    *Commissioner of Patents and Trademarks*